`US005852217A`

United States Patent [19]
Haas et al.

[11] Patent Number: 5,852,217
[45] Date of Patent: Dec. 22, 1998

[54] PROCESS FOR THE PRODUCTION OF PRIMARY AND/OR SECONDARY AMINES FROM OXO COMPOUNDS

[75] Inventors: Thomas Haas, Frankfurt; Dietrich Arntz, Oberursel; Karl-Ludwig Weber, Dieburg; Willi Hofen, Rodenbach; Stefan Wieland, Offenbach, all of Germany

[73] Assignee: Degussa Aktiengesellschaft, Frankfurt, Germany

[21] Appl. No.: 888,394

[22] Filed: Jul. 7, 1997

[30] Foreign Application Priority Data

Jul. 6, 1996 [DE] Germany .......................... 196 27 265.3

[51] Int. Cl.⁶ .................................................. C07C 209/48
[52] U.S. Cl. .............................................................. 564/448
[58] Field of Search ............................................... 564/448

[56] References Cited

U.S. PATENT DOCUMENTS 5,354,831 10/1994 Panster et al. ................................ 528/9
5,679,860 10/1997 Haas et al. ................................ 564/448
5,705,699 1/1998 Witzel ....................................... 564/446

FOREIGN PATENT DOCUMENTS

| 0 042 119 | 12/1981 | European Pat. Off. . |
| 0 449 089 | 10/1991 | European Pat. Off. . |
| 0 623 585 | 11/1994 | European Pat. Off. . |
| 0 659 734 | 6/1995 | European Pat. Off. . |
| 4 426 472 | 2/1995 | Germany . |

*Primary Examiner*—Brian M. Burn
*Attorney, Agent, or Firm*—Wenderoth, Lind & Ponack, L.L.P.

[57] ABSTRACT

This invention relates to a process for the production of primary and/or secondary amines from oxo compounds by catalytic imination of the oxo compound with ammonia or a primary amine and subsequent hydrogenation. Imination proceeds according to the invention in the presence of a novel imination catalyst, namely an organopolysiloxane containing sulphonate groups. This imination catalyst is distinguished by elevated activity. The process is in particular suitable for the production of isophorone diamine from isophorone nitrile, wherein it has proved possible to reduce the content of secondary products and to increase yield.

14 Claims, No Drawings

PROCESS FOR THE PRODUCTION OF PRIMARY AND/OR SECONDARY AMINES FROM OXO COMPOUNDS

DESCRIPTION

This invention relates to a process for the production of primary and/or secondary amines from oxo compounds, which may optionally contain further groups capable of reduction, by imination of the oxo compound and hydrogenation of the imination reaction products. The invention preferably addresses the production of primary mono- and diamines from aldhehydes and ketones and in particular the production of isophorone diamine (3-aminomethyl-3,5,5-trimethyl cyclohexylamine) from isophorone nitrile (3-cyano-3,5,5-trimethyl cyclohexanone).

BACKGROUND OF THE INVENTION

It is known to convert oxo compounds, such as ketones and aldehydes, into primary and/or secondary amines by reductive amination using ammonia or a monoalkylamine and hydrogen. This reaction may be performed in the presence of a single catalyst, i.e. a catalyst which catalyses imination and the subsequent hydrogenation, or in the presence of two catalysts, wherein the first catalyses the imination and the second the hydrogenation. In those cases in which the single stage method using a single catalyst results in an unsatisfactory yield and/or unwanted secondary products, for example the primary alcohol obtainable by direct hydrogenation of the oxo compound, it may be advantageous to perform the reductive amination in two stages. Both single stage processes (c.f. for example EP-A 0 659 734) and two stage processes (c.f. for example EP-B 0 042 119) are known for the production of isophorone diamine from isophorone nitrile. Since it is desired to obtain isophorone diamine as an epoxy resin hardener and as a raw material for the production of isophorone diisocyanate as economically as possible and at elevated purity, there is a requirement for further improved processes.

According to EP 0 042 119, an inorganic or organic ion exchanger in ammonium form is used as an imination catalyst for the conversion reaction of the same generic type of isophorone nitrile into isophorone diamine. A disadvantage of the imination catalysts stated in this document, in which only organic ion exchangers are substantiated, is the thermal and optionally mechanical sensitivity thereof.

In order to remedy the last-stated disadvantages, it has been proposed in EP 0 449 089 to use acidic metal oxides, in particular $Al_2O_3$, $TiO_2$, $SiO_2$ and $ZrO_2$ as an imination catalyst and to perform the reaction in two separate reaction chambers, imination at 20° to 150° C. and 15 to 200 bar and hydrogenation at 60° to 150° C. and 50 to 300 bar. Replication of the process revealed that the proportion of hydroxylamines formed, namely the cis and trans isomers of isophorone amino alcohol (3-aminomethyl-3,5,5-trimethyl cyclohexanol) is very high, thus entailing elaborate purification measures.

When producing isophorone diamine according to DE patent application 195 40 191.3 (corresponding to U.S. Ser. No. 08/739,044 now U.S. Pat. No. 5,679,860) using a special cobalt hydrogenation catalyst (Raney type), it proved necessary additionally to use an imina- tion catalyst in order to minimize levels of hydroxylamines and other unwanted secondary products. When a catalyst combination of the imination catalyst and the cobalt hydrogenation catalyst to reduce the imino group and the nitrile group is used, isophorone diamine is obtained in very good yield and at elevated purity.

EP-A 0 623 585 also discloses a two stage process for the reductive amination of ketones, such as isophorone nitrile. The imination catalyst is activated carbon and the hydrogenation catalyst is a cobalt catalyst containing an alkaline earth metal carbonate and/or lanthanum oxide. From the quantity of activated carbon stated by way of example, catalyst volume is found to be relatively high in relation to the converted (97.7%) isophorone nitrile. This results in high reactor costs. Further disadvantages of this process are incomplete conversion and elevated pressure.

Even when supported heteropolyacids are used as the imination catalyst according to DE-A 44 26 472, it is necessary to use a large volume of imination catalyst, relative to converted isophorone nitrile, an elevated pressure (238 bar) and furthermore a relatively high imination temperature (70° C.). There is consequently a risk of a limited catalyst service life due to deactivation.

DESCRIPTION OF THE INVENTION

The object of the present invention is accordingly to provide another process for the reductive amination of oxo compounds, in particular isophorone nitrile, using an imination catalyst and a hydrogenation catalyst, which process does not exhibit the disadvantages of prior art processes. In particular, it should be possible to perform the process continuously at the lowest possible reaction temperature during the imination stage and, for a given catalyst volume, the process should give rise to a higher reaction rate and higher conversion and thus a lower hydroxylamine content in the crude isophorone diamine product than prior art systems.

A process has been found for the production of primary and/or secondary amines from oxo compounds, which may optionally contain further groups capable of reduction, in particular for the production of isophorone diamine from isophorone nitrile, wherein the oxo compound is iminated in the presence of a imine-forming catalyst in the presence or absence of an organic solvent with excess ammonia for the purpose of producing primary amines or with a lower monoalkylamine for the purpose of producing secondary amines and the resultant reaction products are hydrogenated with hydrogen in the presence of a hydrogenation catalyst at a temperature in the range from 20° to 250° C. and a pressure in the range from 0.5 to 25 MPa, which process is characterized in that an organopolysiloxane containing sulphonate groups and resistant to partial or complete dissolution in the reaction medium is used as the imination catalyst.

Preferred embodiments of the process are also disclosed herein.

The process according to the invention may be used for the production of primary and/or secondary amines from oxo compounds, which are, as is usual, taken to be compounds containing carbonyl groups. The oxo compounds may have one or more carbonyl groups and additionally further reducible groups, such as nitrile groups or olefinic double bonds. The process preferably relates to the production of primary amines from aliphatic, cycloaliphatic, aromatic and heteroaromatic aldehydes and ketones, wherein ammonia acts as the iminating agent in this reaction. A lower monoalkylamine, in particular a ($C_1$ to $C_4$) alkylamine, is used as the iminating agent for the production of secondary amines. The process according to the invention is in particular suitable for the production of primary mono- and diamines from relatively high molecular weight, carbonyl compounds which have a complex structure or are polyfunctional, for which single stage reductive amination results in an unsatisfactory space/time yield, in the formation of unwanted secondary products or in a reduction in catalyst activity. Although oxo compounds having very different structures are obtainable from the process, for example benzylamine from benzaldehyde, furfurylamine from furfurol and isophorone diamine from isophorone nitrile, the process according to the invention is illustrated using the industrially significant production of isophorone diamine from isophorone nitrile by way of example.

The imination catalyst to be used according to the invention preferably comprises products as are described in U.S. Pat. Nos. 4,552,700 and 5,354,831. In these products, the sulphonate group is attached to the organopolysiloxane matrix via an organic group. The organic group between the sulphonate group and the organopolysiloxane matrix is preferably an alkylene group having 1 to 12 C atoms, in particular a propylene group. Explicit reference is made to the above-stated patent documents with regard to the structure and possible variations within this class of substances suitable as imination catalysts. A particularly preferred catalyst substantially consists of units of the formula $HO_3S$—$(CH_2)_3$—$SiO_{3/2}$ . a $SiO_{4/2}$, wherein a is an integer from 4 to 20, in particular 9. The sulphonic acid content of preferred catalysts is preferably between 0.5 and 1.5 mVal/g of the dry catalyst, in particular between 0.5 and 1.0 mVal/g. Where the catalyst is used in a fixed bed reactor, the catalyst is conveniently used in a shaped form, in particular in spherical form. A catalyst substantially comprising spherical particles having a diameter in the range from 0.1 to 2 mm is preferred. A process for the production of such shaped catalysts and the material data themselves are disclosed in U.S. Pat. No. 5,354,831. The shaped articles have an elevated pore volume; the pores are meso- and macropores.

In the imination stage, the imination catalyst may be used either as a suspended catalyst or in the form of a fixed bed arranged in the reactor. The imination catalyst is preferably arranged as a fixed bed. The mixture of substances to be reacted may be charged from beneath, thus keeping the reactor in a flooded state, or the reactor is operated as a trickle bed by introducing the mixture of substances from above.

Conventional hydrogenation catalysts may be used in the hydrogenation stage downstream from the imination stage. These are as generally known for hydrogenating imines and for hydrogenating other reducible groups optionally present in the oxo compound. A hydrogenation catalyst is preferably selected from the range comprising catalysts containing cobalt, nickel, ruthenium and/or other noble metals. Examples of such catalysts are stated in the documents cited above. The hydrogenation catalyst may also be used in the form of a suspended or fixed bed catalyst. Where hydrogenation is performed using a fixed catalyst bed, trickle bed operation is preferred.

The imination reactor is charged with a mixture of substances prepared from the oxo compound for the production of isophorone diamine, i.e. isophorone nitrile, ammonia or, if secondary amines are being produced, a monoalkylamine and, optionally, one or more organic solvents. Ammonia or the monoalkylamine are used in excess. The molar ratio of ammonia or monoalkylamine per carbonyl group of the oxo compound is preferably in the range between approx. 2 and 50. According to a preferred embodiment, the mixture of substances to be charged into the imination reactor also contains an organic solvent, such as in particular an alcohol or ether, wherein methanol is particularly preferred. Imination proceeds at a temperature at which the imination catalyst is resistant to partial dissolution by the reaction mixture, conventionally below 100° C. The temperature is preferably within the range between 0° and 70° C., in particular between 10° and 30° C. The reaction conveniently proceeds at the pressure which is established in the sealed apparatus.

When producing isophorone diamine, the mixture of substances preferably to be charged into the imination reactor contains methanol and 10 to 40 wt. %, in particular 10 to 30 wt. %, of isophorone nitrile as well as 10 to 40 wt. %, preferably 20 to 40 wt. %, of ammonia. Fractions from working up the isophorone diamine by distillation may additionally be added to this mixture of substances, provided that such fractions contain raw materials suitable for the formation of isophorone diamine. In order to increase overall yield, it is convenient to charge the fraction which boils at a temperature above isophorone diamine into the imination stage, which fraction, in addition to isophorone diamine residues, contains 3,3,5-trimethyl-6-imino-7-azabicyclo-[3.2.3]octane as the main product; alternatively, this secondary product fraction may also be added to the hydrogenation stage.

The reaction mixture leaving the imination stage or a mixture of substances containing imination products prepared therefrom is charged into the hydrogenation stage. Hydrogenation is performed under reaction conditions which are known per se. The reaction temperature is conventionally between 20° and 250° C., usually above 50° C. Hydrogenation preferably proceeds at 50° to 150° C., in particular at 90° to 130° C. Depending upon the hydrogenation catalyst used, hydrogenation generally proceeds at a pressure of 0.5 to 25 MPa, in particular at 3 to 10 MPa. Hydrogenation generally proceeds in the presence of or at least a proportion of the ammonia or monoalkylamine used in excess in the imination stage and of the solvent. The reaction mixture leaving the hydrogenation reactor is worked up in a manner known per se. This working up conventionally comprises removing the ammonia or monoalkylamine by distillation and subsequently the solvent and fractional distillation of the crude product.

Surprisingly, the catalyst activity of the imination catalyst to be used according to the invention is substantially higher than that of known prior art catalysts based on organic ion exchangers containing sulphonate groups or acidic metal oxides. Activity is also still greater than that of activated carbon, which performs better than other prior art imination catalysts with regard to the range of secondary products. Further advantages of the imination catalysts to be used according to the invention are that they have an extended service life and moreover do not reduce the activity of the downstream hydrogenation catalyst. When producing isophorone diamine from isophorone nitrile, it additionally proved possible by using the imination catalyst according to the invention distinctly to reduce the content of hydroxyamines, which are taken to be the cis and trans isomers of 3-aminomethyl-3,5,5-trimethyl-cyclohexanol, in comparison with the use of prior art imination catalysts.

EXAMPLE B1 AND COMPARATIVE EXAMPLE
VB1 and VB2

20 ml of an 18 wt. % methanolic isophorone nitrile solution were combined with 20 ml of a 30 wt. % aqueous ammonia solution in a sealed stirred flask at 20° C. 4 ml of imination catalyst were added. The decrease in isophorone nitrile concentration was measured by means of a UV detector.

An organopolysiloxane containing sulphonic acid groups was used in B1 in the form of highly porous spheres having a diameter of 0.1 to 1.4 mm, produced according to U.S. Pat. No. 5,354,831. The catalyst substantially consisted of units of the formula $HO_3S$—$(CH_2)_3$—$SiO_{3/2}$ . 9 $SiO_{4/2}$ and had a sulphonic acid content of 0.9 mVal/g of dry catalyst.

The imination catalyst in VB1 was an organic cation exchanger based on styrene/divinylbenzene and containing sulphonate groups (Dowex® 50WX8 from Dow Chemicals).

The imination catalyst in VB2 was an activated carbon (Norit RAX1 from Norit).

While 35% of the isophorone nitrile had in each case been converted after 15 minutes with the prior art organic cation exchanger and the activated carbon, this conversion was achieved after only 7.5 minutes when the organopolysiloxane containing sulphonate groups according to the invention was used. The imination catalyst according to the invention is thus substantially more active than the prior art imination catalysts.

EXAMPLE B2 AND COMPARATIVE EXAMPLES VB3, VB4, VB5 and VB6

Isophorone nitrile was aminated and reduced with hydrogen in the presence of an excess of ammonia and methanol as solvent in an apparatus comprising an imination reaction and a downstream hydrogenation reactor.

The imination reactor used was a reaction tube filled with 15 ml of imination catalyst, through which a mixture of isophorone nitrile, ammonia and methanol were pumped from the bottom upwards. The temperature in the imination stage was maintained at 25° C.

The imination reactor was charged with a mixture, mixed immediately upstream from the reactor inlet, prepared from 52 ml/h of starting solution (24 wt. % of isophorone nitrile and 76 wt. % of methanol) and 28 ml/h of liquid ammonia. The LHSV value in the imination reactor was thus 5.3 $h^{-1}$.

The hydrogenation reactor used was a reaction tube operated as a trickle bed and containing 150 ml of hydrogenation catalyst. A Raney type activated cobalt catalyst produced according to DE patent application 43 45 265 was used as tablets of a height of 5 mm and a diameter of 3 mm. The hydrogenation reactor was maintained at 100° C. and the pressure set to 6 MPa. The mixture leaving the imination reactor was introduced into the hydrogenation reactor co-currently with hydrogen. The stream of $H_2$ gas was adjusted in such a manner that all the hydrogen was consumed. The liquid leaving the reactor was analyzed.

The imination catalysts used were:

B2: catalyst according to the invention as in B1

VB3: titanium dioxide P25 from Degussa AG as extruded pellets (diameter 1 mm, height 3 to 4 mm)

VB4: Dowex 50WX8 cation exchanger according to VB1

VB5: activated carbon (Norit RAX1) as extruded mouldings (diameter 1 mm, height 3 to 4 mm)

VB6: inorganic ion exchanger zeolite ZSM-5 as cylindrical tablets (height and diameter approx. 2 mm).

According to analysis (GC determination with internal standard) of the reaction mixture leaving the hydrogenation reactor, the proportion of hydroxylamines, relative to the sum of all the products formed from isophorone nitrile, stated in the following Table was obtained, i.e. substantially isophorone diamine, the two isomeric hydroxylamines (cis- and trans-3-aminomethyl-3,5,5-trimethylcyclohexanol), 3,5, 5-trimethyl-6-imino-7-azabicyclo[3.2.1]octane and 2-aza-4, 6,6-trimethylbicyclo-[3.2.]octane.

| Example no. | Quantity of hydroxylamine |
|---|---|
| B2 | 1.0 wt. % |
| VB3 | 4.0 wt. % |
| VB4 | 3.6 wt. % |
| VB5 | 1.6 wt. % |
| VB6 | 8.5 wt. % |

When the imination catalyst according to the invention is used, smaller quantities of hydroxylamines are formed due to the higher conversion in the imination stage. The much higher reaction rate in comparison with activated carbon should also be emphasized. It was furthermore observed that similarly large quantities of hydroxylamines were formed on using zeolite Y and mesoporous zeolite MFI, as were formed in VB6 with zeolite ZSM5.

EXAMPLE B3 AND COMPARATIVE EXAMPLE VB7

An apparatus according to Example B2 was operated under the conditions stated therein for 200 hours, wherein the imination catalyst according to the invention defined in B1 was used on one occasion (=B3) and the activated carbon stated in VB2 was used on the other (=VB7).

Even after 200 hours, analysis of the product mixture in B3 still revealed a hydroxylamine content of 1.0%, relative to the sum of the products formed from isophorone. The yield of isophorone diamine was 94.8% to 95.0% and remained constant over the entire test period.

Analysis of the product mixture in VB7 showed that the proportion of hydroxylamines rose from 1.6 to 2.0% within 200 hours. Moreover, there was a distinct decrease in the hydrogenation activity of the hydrogenation catalyst downstream from the imination reactor; the yield of isophorone diamine fell by 1.5% from 94.3% over this period.

What is claimed is:

1. In a process for the production of a primary amine from an oxo compound selected from the group consisting of aliphatic, cycloaliphatic, aromatic and heteroaromatic aldehydes and ketones, which oxo compound may optionally contain further groups capable of reduction, which comprises iminating the oxo compound in the presence of a imine-forming catalyst and in the presence or absence of an organic solvent with excess ammonia to produce the primary amine and hydrogenating the resultant reaction product with hydrogen in the presence of a hydrogenation catalyst at a temperature in the range from 20° to 250° C. and a pressure in the range from 0.5 to 25 MPa, the improvement wherein
an organopolysiloxane containing sulphonate groups and which is resistant to partial or complete dissolution in the reaction medium is used as the imination catalyst.

2. A process according to claim 1 wherein isophorone diamine is produced from isophorone nitrile.

3. A process according to claim 1, wherein
the imination catalyst is employed in the form of substantially spherical particles containing meso- and macropores and having a diameter in the range from 0.1 to 2 mm.

4. A process according to claim 3, wherein
the imination catalyst has a sulphonate group capacity in the range from 0.5 to 1.5 mVal/g.

5. A process according to claim 4 wherein the range is from 0.75 to 1.0 mVal/g.

6. A process according to claim 2, wherein the imination catalyst is employed in the form of substantially spherical particles containing meso- and macropores and having a diameter in the range from 0.1 to 2 mm.

7. A process according to claim 6, wherein the imination catalyst has a sulphonate group capacity in the range from 0.5 to 1.5 mVal/g.

8. A process according to claim 7 wherein the range is from 0.75 to 1.0 mVal/g.

9. A process according to claim 1, wherein at least one catalyst selected from the group consisting of of catalysts containing cobalt, nickel, ruthenium and/or other noble metals are employed as the hydrogenation catalyst.

10. A process according to claim 2, wherein at least one catalyst selected from the group consisting of of catalysts containing cobalt, nickel, ruthenium and/or other noble metals are employed as the hydrogenation catalyst.

11. A process according to claim 1, wherein imination is performed at a temperature in the range from 0° to 70° C., and hydrogenation is performed at a temperature in the range from 50° to 150° C.

12. A process according to claim 11 wherein imination is performed at a temperature of from 10° to 30° C. and hydrogenation is performed at a temperature of from 90° to 130° C.

13. A process according to claim 2, wherein imination is performed at a temperature in the range from 0° to 70° C., and hydrogenation is performed at a temperature in the range from 50° to 150° C.

14. A process according to claim 13 wherein imination is performed at a temperature of from 10° to 30° C. and hydrogenation is performed at a temperature of from 90° to 130° C.

* * * * *